(12) United States Patent
Yano et al.

(10) Patent No.: US 10,603,649 B2
(45) Date of Patent: Mar. 31, 2020

(54) REACTOR

(71) Applicant: IHI CORPORATION, Tokyo (JP)

(72) Inventors: Akihisa Yano, Tokyo (JP); Tatsuya Oka, Tokyo (JP); Hiroyuki Kamata, Tokyo (JP); Shigeki Sakakura, Tokyo (JP); Nobuyuki Honma, Tokyo (JP); Yusuke Takeuchi, Tokyo (JP)

(73) Assignee: IHI CORPORATION, Tokyo (JP)

( * ) Notice: Subject to any disclaimer, the term of this patent is extended or adjusted under 35 U.S.C. 154(b) by 0 days.

(21) Appl. No.: 15/821,049

(22) Filed: Nov. 22, 2017

(65) Prior Publication Data

US 2018/0093242 A1  Apr. 5, 2018

Related U.S. Application Data

(63) Continuation of application No. PCT/JP2016/066993, filed on Jun. 8, 2016.

(30) Foreign Application Priority Data

Jun. 8, 2015 (JP) .................................. 2015-115655

(51) Int. Cl.
*B01J 19/24* (2006.01)
*F28D 9/00* (2006.01)
(Continued)

(52) U.S. Cl.
CPC ......... *B01J 12/007* (2013.01); *B01J 19/0013* (2013.01); *B01J 19/245* (2013.01);
(Continued)

(58) Field of Classification Search
CPC ...... B01J 12/007; B01J 19/0013; B01J 19/24; B01J 19/2438; C01B 3/38; C01B 3/384;
(Continued)

(56) References Cited

U.S. PATENT DOCUMENTS 2,684,390 A  7/1954  Bills
4,983,366 A  1/1991  Deller et al.
(Continued)

FOREIGN PATENT DOCUMENTS

CA  2 899 697 A1  8/2014
CN  101367695 A  2/2009
(Continued)

OTHER PUBLICATIONS

Machine translation for CN201978726 (U)—Nov. 5, 2018.*
(Continued)

*Primary Examiner* — Huy Tram Nguyen

(57) ABSTRACT

A reactor includes: a main reactor core including main reaction flow channels through which the raw material fluid flows, and main temperature control flow channels through which the heat medium flows along a flow direction of the raw material fluid flowing in the main reaction flow channel; and a pre-reactor core including pre-reaction flow channels of which an outlet side connects with an inlet side of the main reaction flow channels and through which the raw material fluid flows, and pre-temperature control flow channels of which an inlet side connects with an outlet side of the main reaction flow channels and through which the product serving as the heat medium flows along a flow direction of the raw material fluid flowing in the pre-reaction flow channel.

10 Claims, 10 Drawing Sheets

(51) Int. Cl.
| | |
|---|---|
| B01J 12/00 | (2006.01) |
| F28F 3/04 | (2006.01) |
| F28F 3/00 | (2006.01) |
| C01B 3/38 | (2006.01) |
| B01J 19/00 | (2006.01) |
| C01B 3/48 | (2006.01) |
| C07C 1/04 | (2006.01) |
| F28D 21/00 | (2006.01) |

(52) U.S. Cl.
CPC ......... *B01J 19/249* (2013.01); *B01J 19/2485* (2013.01); *C01B 3/38* (2013.01); *C01B 3/384* (2013.01); *C01B 3/48* (2013.01); *C07C 1/041* (2013.01); *F28D 9/0037* (2013.01); *F28D 9/0093* (2013.01); *F28F 3/00* (2013.01); *F28F 3/048* (2013.01); *B01J 2208/0053* (2013.01); *B01J 2208/00212* (2013.01); *B01J 2208/022* (2013.01); *B01J 2219/00094* (2013.01); *B01J 2219/00159* (2013.01); *B01J 2219/2411* (2013.01); *B01J 2219/2414* (2013.01); *B01J 2219/2453* (2013.01); *B01J 2219/2462* (2013.01); *B01J 2219/2467* (2013.01); *C01B 2203/0233* (2013.01); *C01B 2203/0238* (2013.01); *C01B 2203/0283* (2013.01); *C01B 2203/0833* (2013.01); *C01B 2203/0883* (2013.01); *C01B 2203/1241* (2013.01); *F28D 2021/0022* (2013.01)

(58) Field of Classification Search
CPC ......... C07C 1/041; F28D 9/00; F28D 9/0037; F28D 9/0093; F28F 3/00; F28F 3/048
USPC .......................................... 422/633
See application file for complete search history.

(56) References Cited

U.S. PATENT DOCUMENTS

| | | | |
|---|---|---|---|
| 6,143,943 | A | 11/2000 | Oroskar |
| 6,159,358 | A | 12/2000 | Mulvaney, III |
| 2002/0172846 | A1 | 11/2002 | Hagan et al. |
| 2004/0034266 | A1 | 2/2004 | Brophy et al. |
| 2004/0076562 | A1 | 4/2004 | Manzanec et al. |
| 2006/0112636 | A1 | 6/2006 | Chellappa |
| 2006/0199051 | A1 | 9/2006 | Bai et al. |
| 2009/0004076 | A1 | 1/2009 | Brophy et al. |
| 2009/0311150 | A1 | 12/2009 | Cho et al. |
| 2011/0152597 | A1 | 6/2011 | Brophy et al. |
| 2012/0142789 | A1 | 6/2012 | Morgan et al. |
| 2013/0032490 | A1 | 2/2013 | Le Gallo et al. |
| 2014/0140896 | A1* | 5/2014 | Moon .................. B01J 19/0093 422/162 |
| 2016/0144336 | A1* | 5/2016 | Hamada .................... C01B 3/38 422/601 |

FOREIGN PATENT DOCUMENTS

| | | |
|---|---|---|
| CN | 201978726 U | 9/2011 |
| JP | S46-001158 A | 9/1971 |
| JP | S58-010583 U1 | 1/1983 |
| JP | H02-083017 A | 3/1990 |
| JP | H10-034106 A | 2/1998 |
| JP | 2004-532507 A | 10/2004 |
| JP | 2005-529950 A | 10/2005 |
| JP | 2006-505387 A | 2/2006 |
| JP | 2008-532252 A | 8/2008 |
| JP | 2009-136841 A | 6/2009 |
| JP | 2013-503031 A | 1/2013 |
| JP | 2013-522459 A | 6/2013 |
| JP | 2014-526961 A | 10/2014 |
| JP | 2014-526962 A | 10/2014 |
| WO | 2003/106386 A2 | 12/2003 |
| WO | 2006/043642 A1 | 4/2006 |
| WO | 2013/013077 A2 | 1/2013 |
| WO | 2013/013083 A2 | 1/2013 |
| WO | 2015/037597 A1 | 3/2015 |

OTHER PUBLICATIONS

International Search Report received for PCT Patent Application No. PCT/JP2016/066993 dated Aug. 30, 2016, 4 pages (2 pages of English translation of International Search Report, and 2 pages of International Search Report).

The Japan Petroleum Institute, "Petroleum Refinery Process," Kodansha Ltd., 1998, pp. 314-318.

Taiwan Patent Office, Office Action and Search Report, issued in TW Patent Application No. 105118228, which is a Taiwanese counterpart of JP Appl. Ser. No. 2015-115655, dated Apr. 12, 2017, 8 pages (7 pages of Office Action and 1 page of Search Report).

Japan Patent Office, "Notice of Reasons for Refusal," issued in Japanese Patent Application No. 2017-523660, which is a Japanese counterpart of U.S. Appl. No. 15/821,049, dated Oct. 9, 2018, 5 pages (2 pages of English translation of Office Action, and 3 pages of original Office Action).

European Patent Office, extended European search report, issued in European Patent Application No. 16 807 497.9, which is a European counterpart of U.S. Appl. No. 15/821,049, dated Nov. 16, 2018, 8 pages.

Intellectual Property Office of Singapore, "Search Report and Written Opinion," issued in Singapore Patent Application No. 11201709722T, which is a Singaporean counterpart of U.S. Appl. No. 15/821,049, dated Nov. 13, 2018, 8 pages.

Japan Patent Office, "Office Action", issued in Japanese Patent Application No. 2017-523660, which is a Japanese counterpart of U.S. Appl. No. 15/821,049, dated May 21, 2019, 3 pages.

* cited by examiner

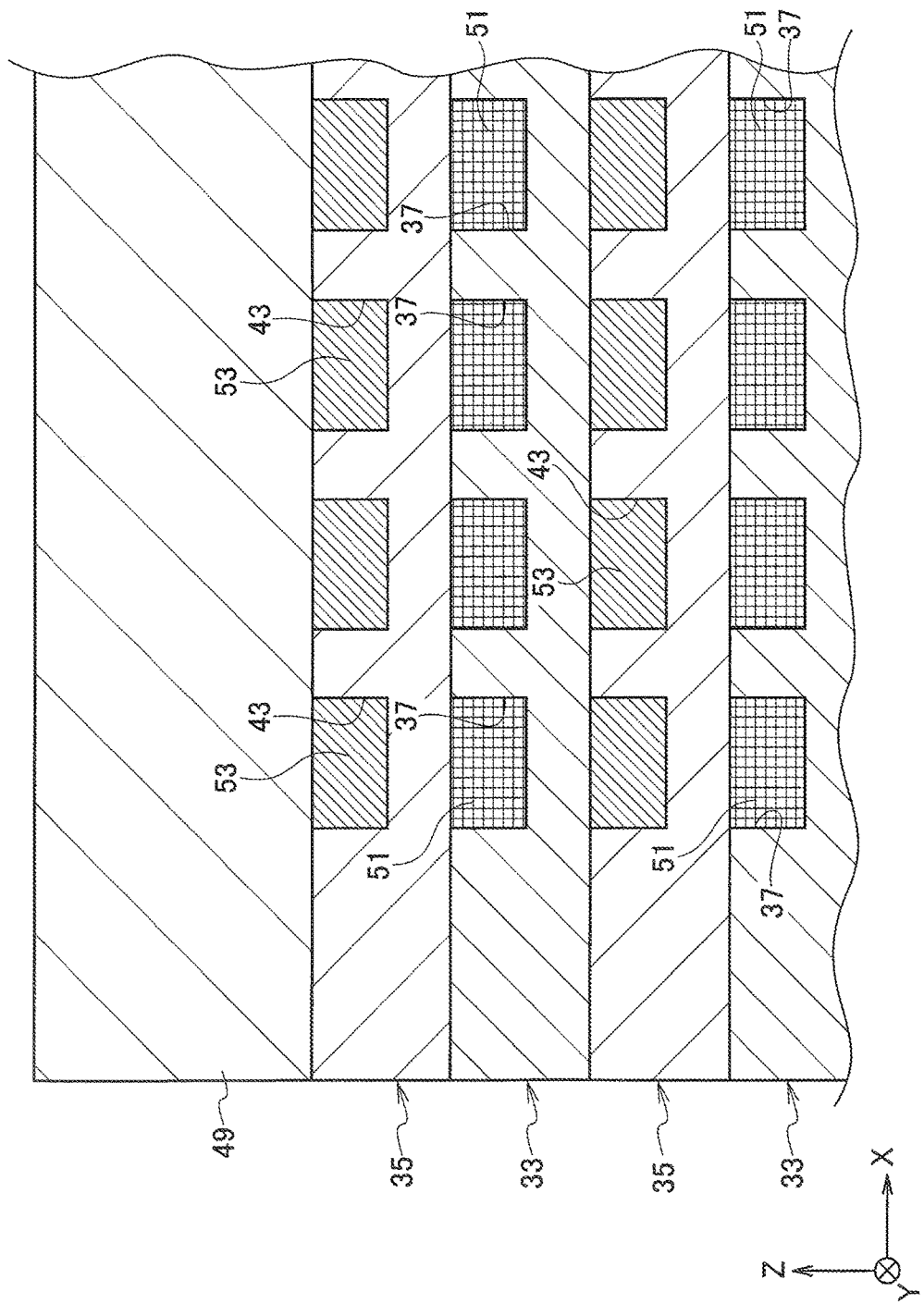

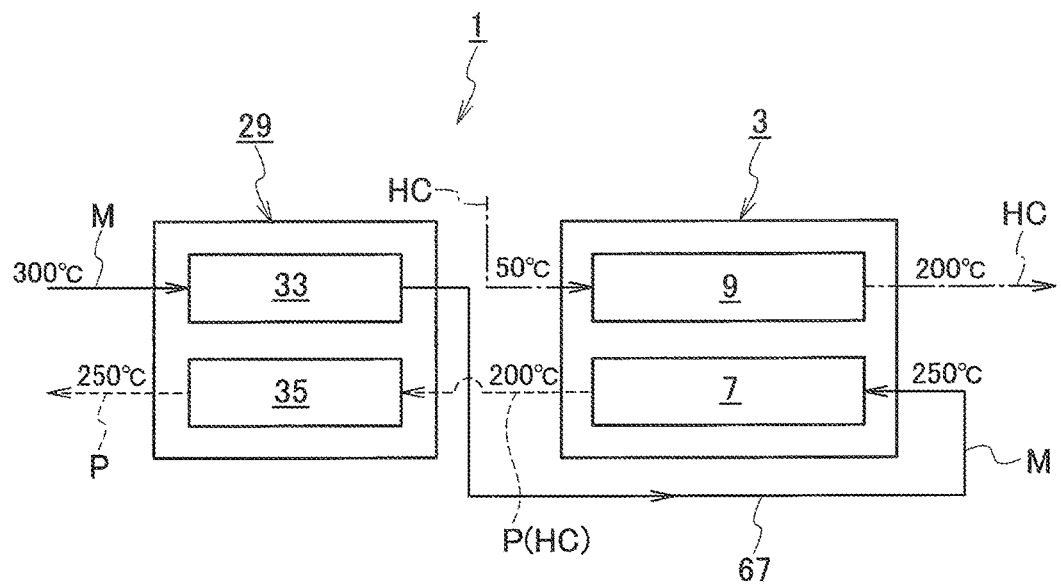
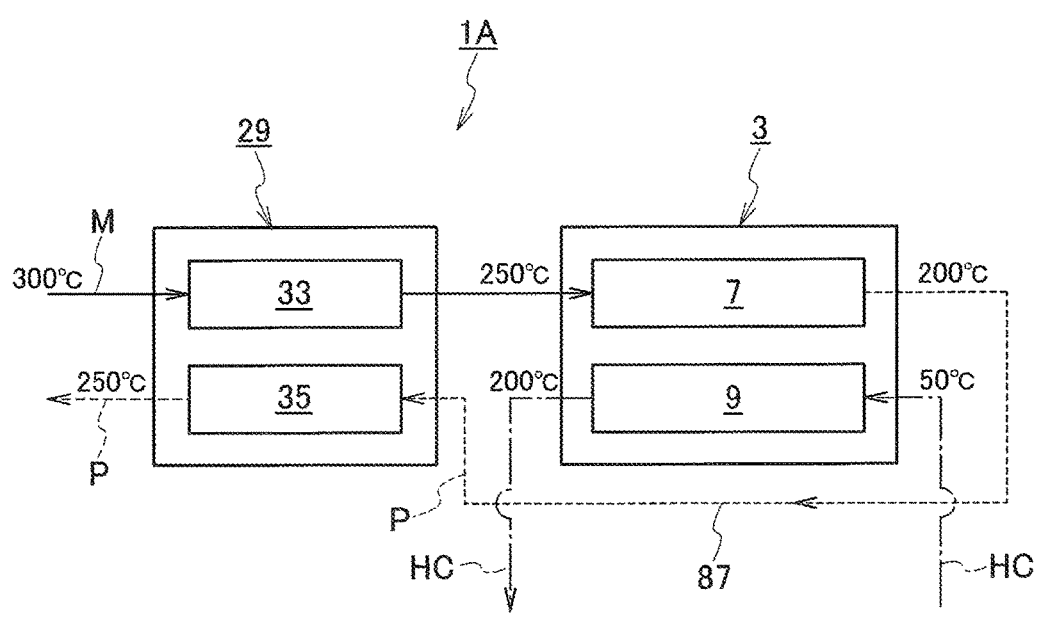

REACTOR

CROSS REFERENCE TO RELATED APPLICATIONS

This application is a continuation application of International Application No. PCT/JP2016/066993, filed on Jun. 8, 2016, which claims priority to Japanese Patent Application No. 2015-115655, filed on Jun. 8, 2015, the entire contents of which are incorporated by reference herein.

BACKGROUND

1. Technical Field

Embodiments described herein relate to a reactor for causing a reaction of a raw material fluid (a reaction fluid) by a heat exchange between the raw material fluid and a heat medium to generate a product (a reaction product).

2. Description of the Related Art

For example, a reactor used for a hydrogen production process includes a reactor core. The reactor core includes reaction flow channels through which a raw material fluid containing methane gas and steam flows, and temperature control flow channels (heating flow channels) through which a heat medium such as flue gas flows. In the configuration described above, the raw material fluid and the heat medium are supplied to the reactor core, so that the raw material fluid flows through the reaction flow channels and the heat medium flows through the temperature control flow channels. The heat exchange is then carried out between the raw material fluid and the heat medium to cause a reaction (an endothermic reaction) of the raw material fluid, so as to produce a product containing hydrogen and carbon monoxide (refer to Journal of the Japan Petroleum Institute, "Petroleum Refinery Process"; Kodansha, p. 314-318, (May 20, 1998) (Non-Patent Literature 1)). Japanese Translation of PCT International Application Publication No. 2006-505387 (Patent Literature 1) discloses a reactor having the configuration described above.

SUMMARY

In order to reduce the time in which a product P remains at extremely high temperature, as high as a temperature range (approximately 400 to 700° C.) of metal dusting, for example, the product P needs to be cooled immediately outside the reactor. The heat of the product P is recovered by a heat exchange between the product P and water (refrigerant) in a quenching drum (heat recovery boiler) placed outside the reactor, while steam serving as part of the raw material fluid is produced as a by-product. As the amount of heat recovered from the product by the quenching drum increases, namely, as the amount of heat recovered from the product outside the reactor increases, heat energy (input energy) of the heat medium supplied to the reactor increases and an excessive amount of steam is produced. As a result, the energy efficiency of the entire plant may deteriorate.

It is noted that not only a reactor used for a hydrogen production process but also other types of reactor have the same problems as described above.

One object of the present disclosure is to provide a reactor capable of improving energy efficiency in an entire plant.

A reactor according to an aspect of the present disclosure causes a reaction of a raw material fluid (a reaction fluid) by a heat exchange between the raw material fluid and a heat medium to generate a product (a reaction product), the reactor including: a main reactor core including a main reaction flow channel through which the raw material fluid flows, and a main temperature control flow channel (a heating flow channel) through which the heat medium flows along a flow direction of the raw material fluid flowing in the main reaction flow channel; and a pre-reactor core including a pre-reaction flow channel of which an outlet side connects with an inlet side of the main reaction flow channel and through which the raw material fluid flows, and a pre-temperature control flow channel (a pre-heating flow channel) of which an inlet side connects with an outlet side of the main reaction flow channel and through which the product serving as the heat medium flows along a flow direction of the raw material fluid flowing in the pre-reaction flow channel.

As used herein, the term "inlet side" denotes an inlet side of the flow direction of the raw material fluid, the product or the heat medium, and the term "outlet side" denotes an outlet side of the flow direction of the raw material fluid, the product or the heat medium.

According to the present disclosure, the raw material fluid is supplied to the pre-reactor core, so that the raw material fluid flows through the main reaction flow channels via the pre-reaction flow channels. In addition, the heat medium is supplied to the main reactor core, so that the heat medium flows through the main temperature control flow channels along the flow direction (for example, in the counter or same direction) of the raw material fluid flowing in the main reaction flow channels. The heat exchange is then carried out between the raw material fluid and the heat medium, so as to increase the temperature of the raw material fluid sufficient to cause a reaction of the raw material fluid, so as to produce a product.

As described above, the raw material fluid supplied to the pre-reactor core flows through the pre-reaction flow channels. The product led out of the main reaction flow channels flows through the pre-temperature control flow channels along the flow direction (for example, in the counter or same direction) of the raw material fluid flowing in the pre-reaction flow channels. The heat exchange is then carried out between the product serving as a heat medium and the raw material fluid, so as to preheat the raw material fluid in the pre-reactor core and cool the product.

Since the product can be cooled in the pre-reactor core, the reactor can reclaim the heat to decrease the temperature of the product, so as to prevent an increase in the amount of the heat recovered from the product outside the reactor.

According to the present disclosure, heat energy (input energy) of the heat medium supplied to the reactor can be reduced, and an excessive amount of steam generated outside the reactor can be suppressed, so as to improve the energy efficiency in the entire plant.

BRIEF DESCRIPTION OF THE DRAWINGS

FIG. 8 is an enlarged view on arrow VIII of FIG. 7

FIG. 10A is a block diagram of the reactor according to one embodiment.

FIG. 10B is a block diagram of a reactor according to another embodiment.

DESCRIPTION OF THE EMBODIMENTS

One embodiment and other embodiments of the present disclosure will be described below with reference to the drawings.

Figure 1:
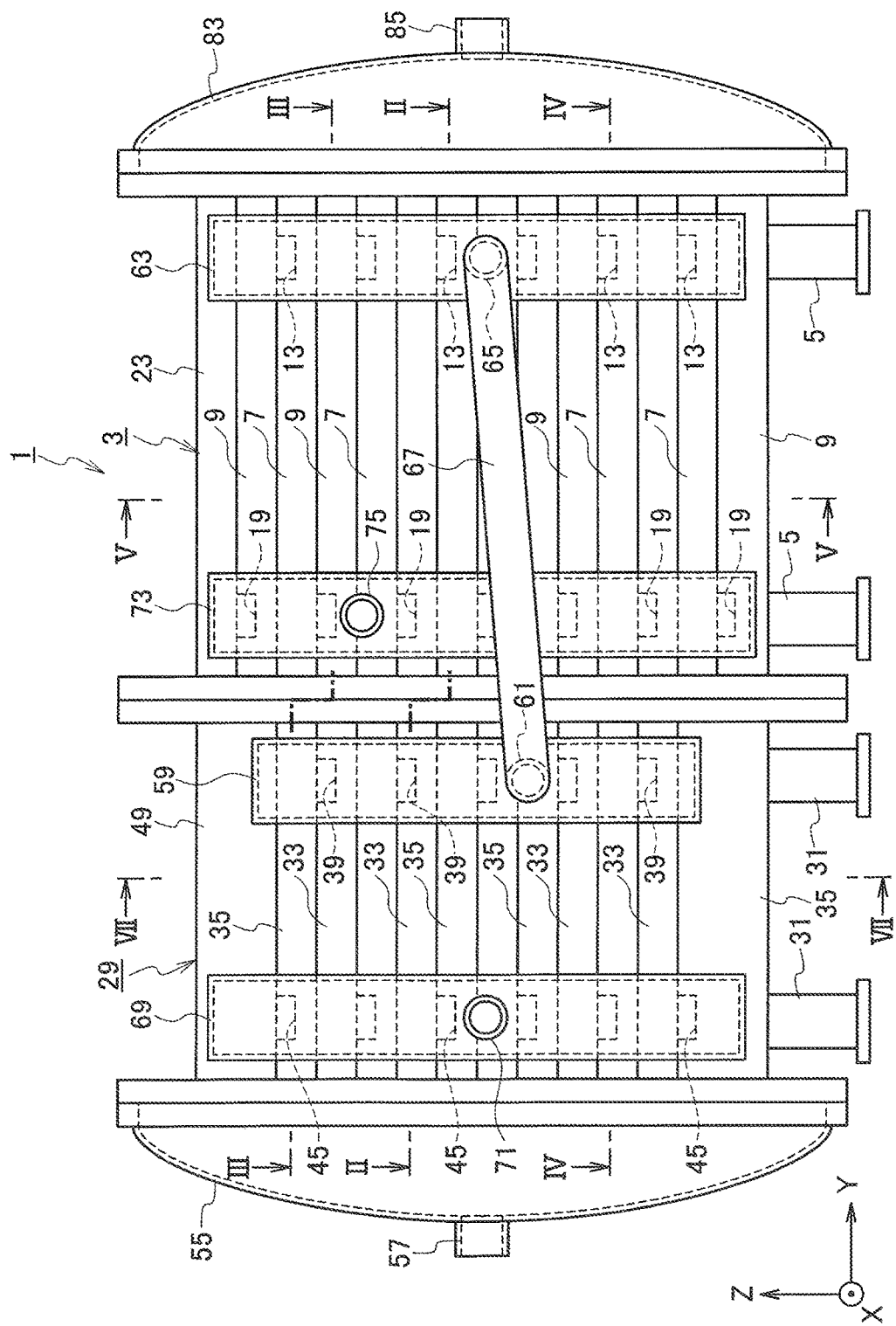
FIG. 1 is a schematic front view of a reactor according to one embodiment of the present disclosure.
Figure 2:
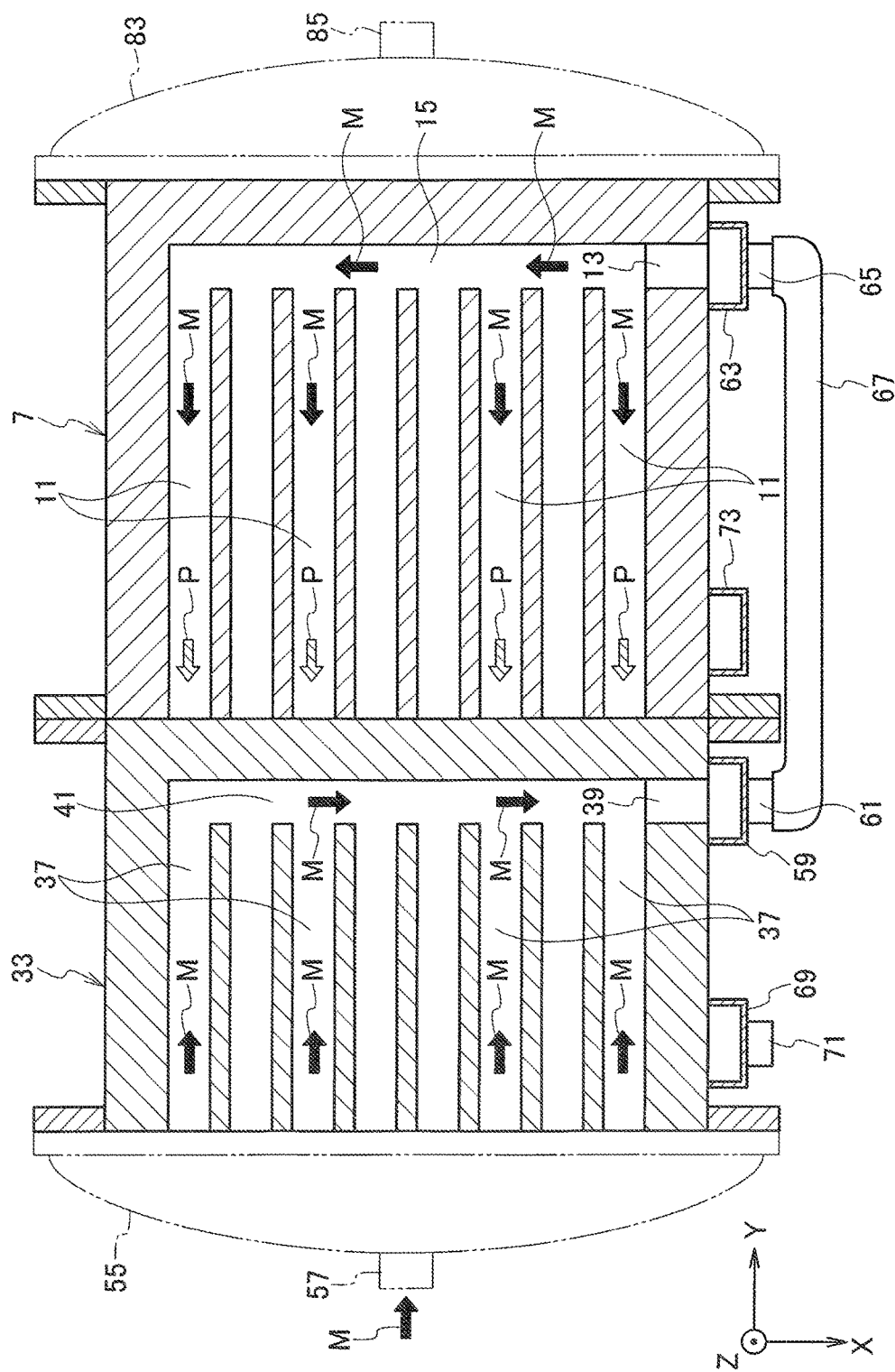
FIG. 2 is a cross-sectional view taken along line of FIG. 1.

As shown in FIG. 1, a reactor 1 according to the present embodiment causes a reaction of a raw material fluid M by a heat exchange between the raw material fluid M (see FIG. 2) and a heat medium HC (see FIG. 3), so as to produce a product P (see FIG. 2). Before a specific configuration of the reactor 1 is described, the reaction of the raw material fluid M is briefly described below.

The reaction of the raw material fluid M includes two types: an endothermic reaction caused by heating the raw material fluid M and an exothermic reaction caused by cooling the raw material fluid M. Examples of the former reaction (the endothermic reaction) include a steam reforming reaction of methane as represented by the following chemical equation (1), and a dry reforming reaction of methane as represented by the following chemical equation (2)

$$CH_4 + H_2O \rightarrow 3H_2 + CO \quad (1)$$

$$CH_4 + CO_2 \rightarrow 2H_2 + 2CO \quad (2)$$

Examples of the latter reaction (the exothermic reaction) include a shift reaction as represented by the following chemical equation (3), a methanation reaction as represented by the following chemical equation (4), and a Fischer tropsch synthesis reaction as represented by the following chemical equation (5).

$$CO + H_2O \rightarrow CO_2 + H_2 \quad (3)$$

$$CO + 3H_2 \rightarrow CH_4 + H_2O \quad (4)$$

$$(2n+1)H_2 + nCO \rightarrow C_nH_{2n+2} + nH_2O \quad (5)$$

The reaction of the raw material fluid M is not limited to the steam reforming reaction of methane and the like, and other examples thereof include an acetylation reaction, an addition reaction, an alkylation reaction, a dealkylation reaction, a hydrodealkylation reaction, a reductive alkylation reaction, an amination reaction, an aromatization reaction, an arylation reaction, a self-heating reforming reaction, a carbonylation reaction, a decarbonylation reaction, a reductive carbonylation reaction, a carboxylation reaction, a reductive carboxylation reaction, a reductive coupling reaction, a condensation reaction, a cracking reaction, a hydrocracking reaction, a cyclization reaction, a cyclo-oligomerization reaction, a dehalogenation reaction, a dimerization reaction, an epoxidation reaction, an esterification reaction, an exchange reaction, a halogenation reaction, a hydrohalogenation reaction, a homologation reaction, a hydration reaction, a dehydration reaction, a hydrogenation reaction, a dehydrogenation reaction, a hydrocarboxylation reaction, a hydroformylation reaction, a hydrogenolysis reaction, a hydrometalation reaction, a hydrosilylation reaction, a hydrolyzation reaction, a hydroprocessing reaction, an isomerization reaction, a methylation reaction, a demethylation reaction, a substitution reaction, a nitration reaction, an oxidation reaction, a partial oxidation reaction, a polymerization reaction, a reduction reaction, a reverse water-gas shift reaction, a sulfonation reaction, a telomerization reaction, a transesterification reaction, and a trimerization reaction.

The heat medium HC used may be high-temperature gas such as flue gas, water, and a refrigerant, and selected as appropriate depending on the reaction type and conditions of the raw material fluid M. For example, when the reaction of the raw material fluid M is a steam reforming reaction of methane, the heat medium HC used is high-temperature gas such as flue gas. When the reaction of the raw material fluid M is a dry reforming reaction of methane, the heat medium HC used is high-temperature gas or the like. When the reaction of the raw material fluid M is a shift reaction, the heat medium HC used is oil, water (including steam), molten salt, or the like. When the reaction of the raw material fluid M is a methanation reaction, the heat medium HC used is oil, water (including steam), molten salt, or the like. When the reaction of the raw material fluid M is a Fischer tropsch synthesis reaction, the heat medium HC used is water (including steam) or the like.

Figure 3:
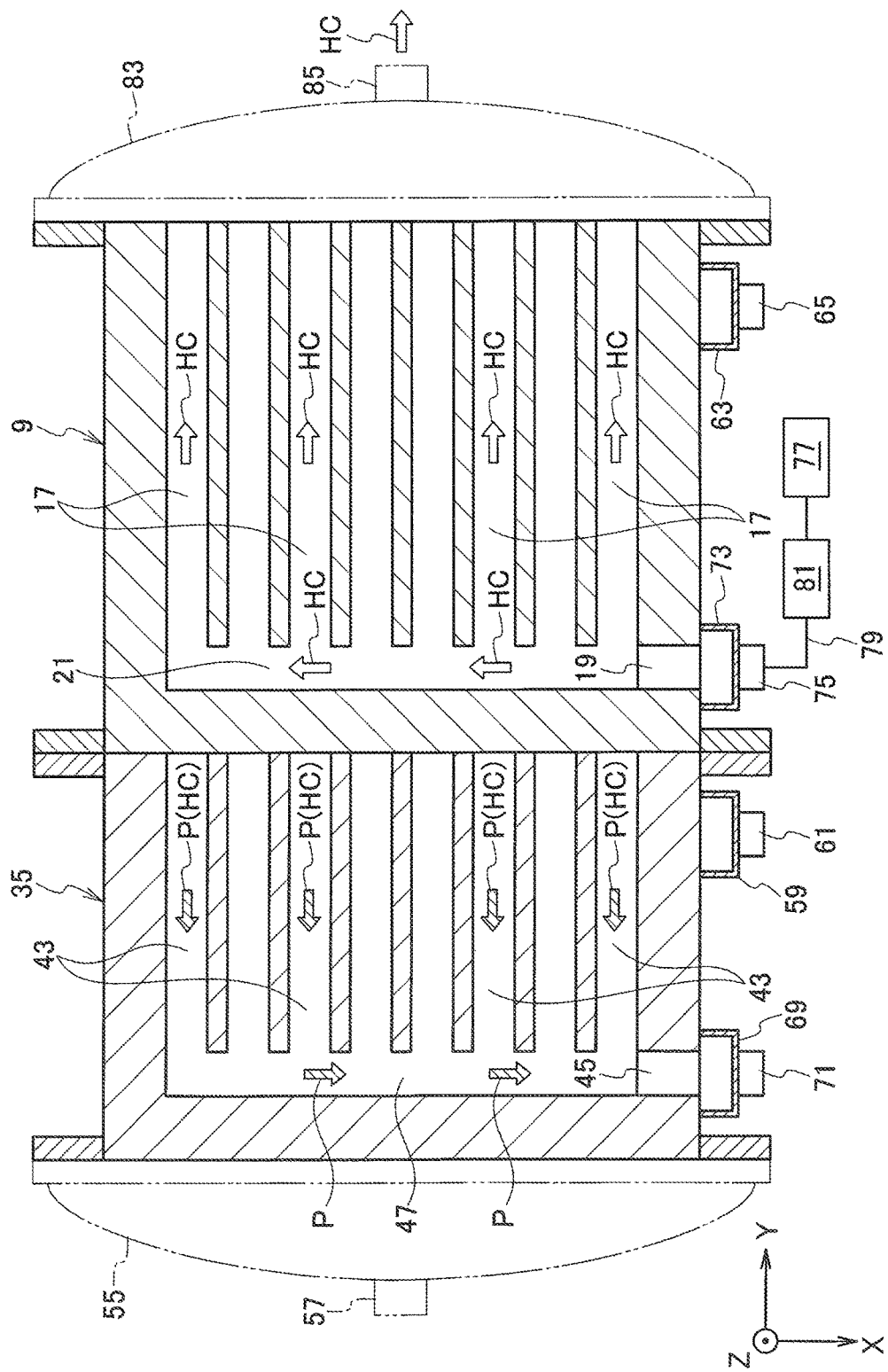
FIG. 3 is a cross-sectional view taken along line III-III of FIG. 1.
Figure 5:
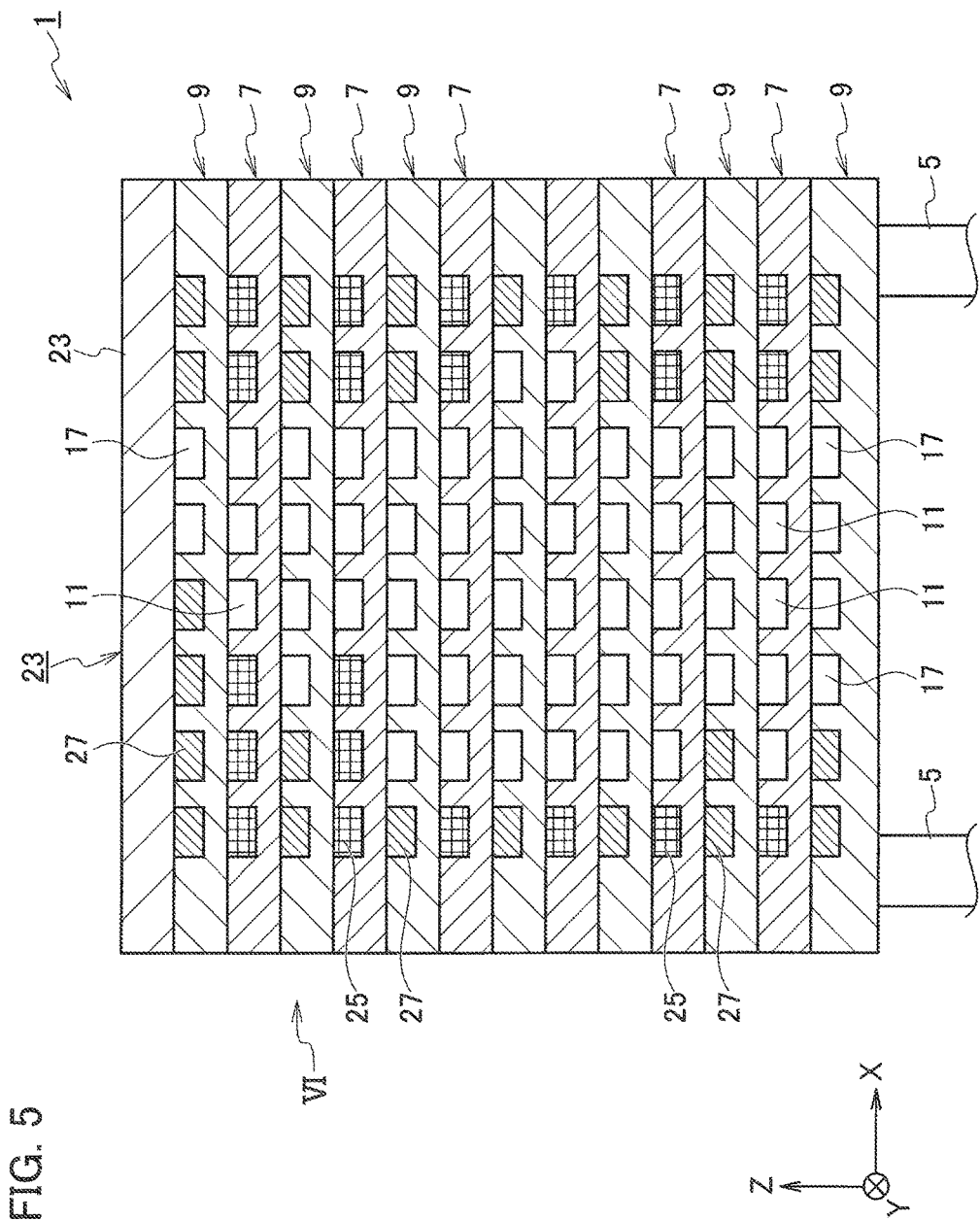
FIG. 5 is a cross-sectional view taken along line V-V of FIG. 1.
Figure 7:
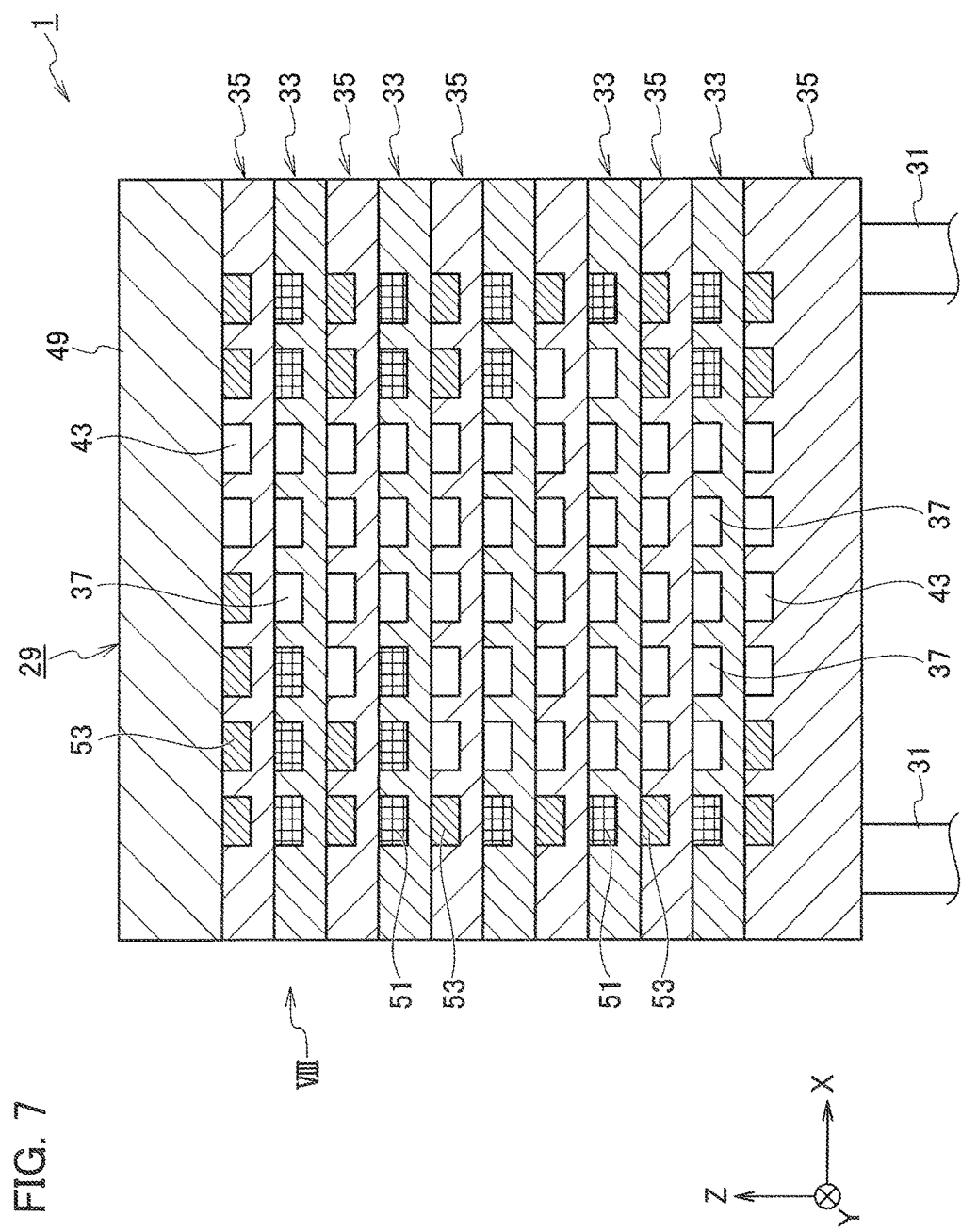
FIG. 7 is an enlarged cross-sectional view taken along line VII-VII of FIG. 1.
Figure 9A:
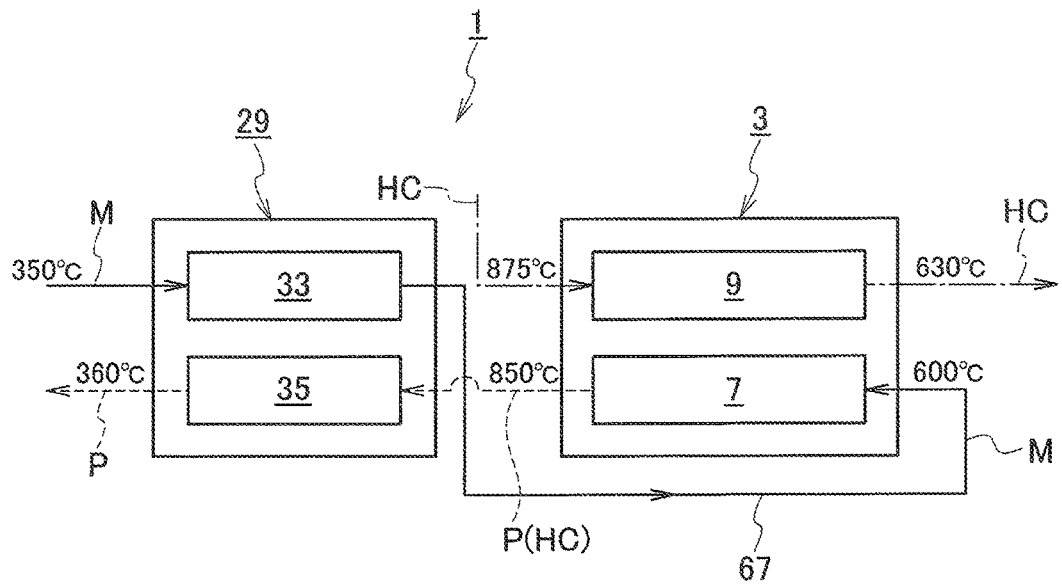
FIG. 9A is a block diagram of the reactor according to one embodiment.
Figure 9B:
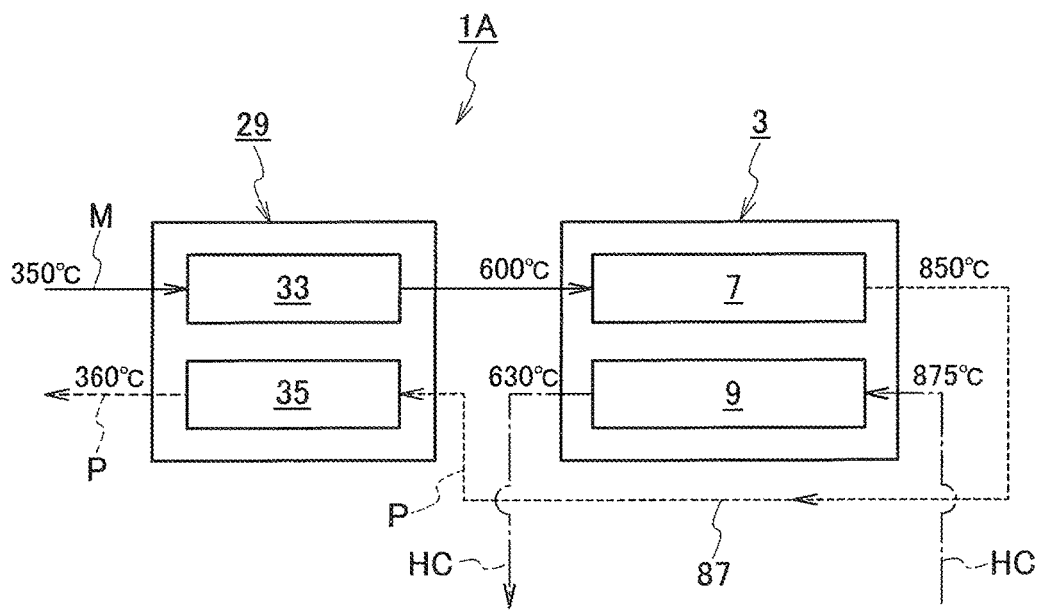
FIG. 9B is a block diagram of a reactor according to another embodiment.

The specific configuration of the reactor 1 is described below. FIG. 2 omits the illustration of main catalyst members and pre-catalyst members. FIG. 3 omits the illustration of main fins and pre-fins. FIG. 5 schematically illustrates only part of the main catalyst members and part of the main fins. FIG. 7 schematically illustrates only part of the pre-catalyst members and part of pre-fins. FIG. 9A and FIG. 9B each illustrate temperature conditions during operation in a case in which the reaction of the raw material fluid is an endothermic reaction. FIG. 10A and FIG. 10B each illustrate temperature conditions during operation in a case in which the reaction of the raw material fluid is an exothermic reaction.

As shown in FIG. 1 and FIG. 5, the reactor 1 includes a main reactor core 3 for causing a reaction of the raw material fluid M to produce a product P. The main reactor core 3 is installed at an appropriate position with a plurality of supporting pillars 5. The main reactor core 3 includes a plurality of (multiple) rectangular main reactor structures (main reactor members) 7 for providing a reaction space for the raw material fluid M (for causing a reaction of the raw material fluid M), and a plurality of (multiple) rectangular main temperature control structures (main temperature control members) 9. The main reactor structures 7 and the main temperature control structures 9 are alternately stacked in the vertical direction (the height direction of the reactor 1 (the Z direction)). The specific configuration of each of the main reactor structures 7 and the main temperature control structures 9 is described below.

FIG. 2 to FIG. 5 illustrate the main reactor structure 7 made of an iron alloy such as stainless steel, or a nickel alloy such as Inconel alloy 625, Inconel alloy 617, and Haynes alloy 230 (examples of heat-resistant alloys). A plurality of main reaction flow channels 11 through which the raw material fluid M flows in the left direction are arranged at regular intervals in the front-rear direction (the depth direction of the reactor 1 (the X direction)) on one surface (the upper surface) of the main reactor structure 7. The respective main reaction flow channels 11 extend in the lateral direction (the width direction of the reactor 1 (the Y direction)), and have a channel length (a length in the lateral direction) which is set at approximately several tens of centimeters in the present embodiment, for example. The right side of the main reaction flow channels 11 corresponds to the inlet side (the introduction side) of the flow direction of the raw material fluid M. The left side of the main reaction flow channels 11 corresponds to the outlet side (the leading-out side) of the flow direction of the raw material fluid M or the product P, and is open so as to lead the raw material fluid M out of the main reaction flow channels 11.

The respective main reaction flow channels 11 have a rectangular shape in cross section. For example, in the present embodiment, the width of the main reaction flow channels 11 is set at 2 to 60 mm, and the height of the main reaction flow channels 11 is set at 1 to 10 mm, preferably 4 to 8 mm.

A raw material introduction port 13 for introducing the raw material fluid M therefrom is provided on the right side on the front surface of the main reactor structure 7. A main reaction connection flow channel 15 by which the raw material introduction port 13 connects with the plural main reaction flow channels 11 on the right side (on the inlet side) is provided on the right side on one surface of the main reactor structure 7. The main reaction connection flow channel 15 extends in the front-rear direction.

The main reactor core 3 is schematically illustrated. For example, the main reactor core 3 includes several tens of main reactor structures 7 and several tens of main reaction flow channels 11 in each main reactor structure 7 in the present embodiment. The number of the main reaction connection flow channel 15 may be changed depending on the number of the main reaction flow channels 11. The maximum pressure in the respective main reaction flow channels 11 when the reactor 1 is in operation is set at a predetermined level in a range of 0.0 to 20.0 MPaG which varies depending on the reaction type and conditions of the raw material fluid M.

The main temperature control structure 9 is made of the same material as the main reactor structure 7. A plurality of main temperature control flow channels (heating flow channels) 17 through which the heat medium HC flows along the flow direction of the raw material fluid M in the main reaction channels 11 (in the right direction opposite to the flow direction (in the counter flow direction)) are arranged at regular intervals in the front-rear direction on one surface of the main temperature control structure 9. The flow direction of the heat medium HC with respect to the flow direction of the raw material fluid M in the main reaction channels 11 includes not only the exactly defined direction but also a direction allowing an inclination to some extent under the conditions in Which the effects of the present embodiment can be achieved. The respective main temperature control flow channels 17 extend in the lateral direction, and have a channel length (a length in the lateral direction) which is set at approximately several tens of centimeters in the present embodiment, for example. The left side of the main temperature control flow channels 17 corresponds to the inlet side (the introduction side) of the flow direction of the heat medium HC. The right side of the main temperature control flow channels 17 corresponds to the outlet side (the leading-out side) of the flow direction of the heat medium HC, and is open so as to lead the heat medium HC out of the main temperature control flow channels 17.

The respective main temperature control flow channels 17 have a rectangular shape in cross section. For example, in the present embodiment, the width of the main temperature control flow channels 17 is set at 2 to 60 mm, and the height of the temperature control flow channels 17 is set at 1 to 10 mm, preferably 4 to 8 mm. The main temperature control flow channels 17 are opposed to the corresponding main reaction flow channels 11 in the vertical direction.

A heat medium introduction port 19 for introducing the heat medium HC therefrom is provided on the left side on the front surface of the main temperature control structure 9. A main temperature control connection flow channel 21 by which the heat medium introduction port 19 connects with the plural main temperature control flow channels 17 on the left side (on the inlet side) is provided on the left side on one surface of the main temperature control structure 9. The main temperature control connection flow channel 21 extends in the front-rear direction.

As described above, the main reactor core 3 is schematically illustrated. For example, the main reactor core 3 includes several tens of main temperature control structures 9 and several tens of main temperature control flow channels 17 in each main temperature control structure 9 in the present embodiment. The number of the main temperature control connection flow channel 21 may be changed depending on the number of the main temperature control flow channels 17. The maximum pressure in the respective main temperature control flow channels 17 when the reactor 1 is in operation is set at a predetermined level in a range of 0.0 to 20.0 MPaG which varies depending on the reaction type and conditions of the raw material fluid M.

As shown in FIG. 5, the lowermost main temperature control structure 9 is thicker than the other main temperature control structures 9. The respective main temperature control structures 9 other than the lowermost main temperature control structure 9 have the same dimensions as the main reactor structures 7. The uppermost main temperature control structure 9 is provided with a main lid structure (a main lid member) 23 having a rectangular plate shape and covering the main temperature control flow channels 17.

Figure 6:
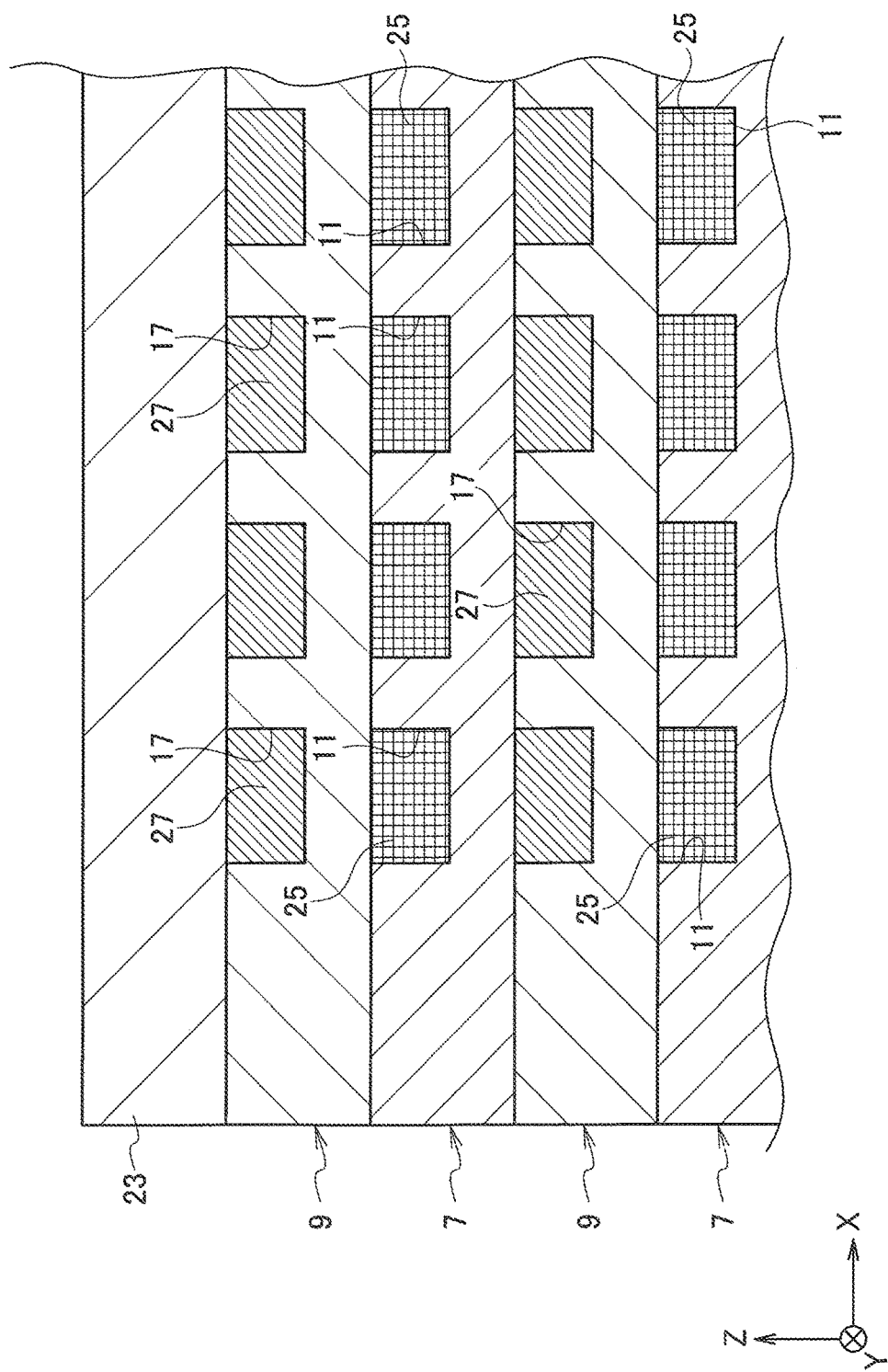
FIG. 6 is an enlarged view on arrow VI of FIG. 5.

As shown in FIG. 5 and FIG. 6, a main catalyst member 25 supporting a catalyst for promoting the reaction of the raw material fluid M is removably provided in the respective main reaction channels 11. The main catalyst member 25 is made of stainless steel, for example, and extends in the lateral direction. The main catalyst member 25 has a wave-like shape in cross section, for example. The catalyst is selected as appropriate depending on the type of the reaction of the raw material fluid M. When the reaction of the raw material fluid M is a steam reforming reaction of methane, the catalyst used is one or more kinds of metal selected from nickel (Ni), platinum (Pt), ruthenium (Ru), rhodium (Rh), palladium (Pd), cobalt (Co), rhenium (Re), and iridium (Ir). The catalyst may be applied on the respective main reaction channels 11 (as an example of supporting methods), instead of the catalyst member 25 removably provided in the respective main reaction channels 11.

A pair of main fins (main baffles) 27 is removably provided in the respective main temperature control flow channels 17. The paired fins 27 are laid on top of each other in the vertical direction. The respective fins 27 are made of stainless steel, for example, and extend in the lateral direction. The respective fins 27 have a wave-like shape in cross section, for example.

As shown in FIG. 1 and FIG. 7, a pre-reactor core 29 for preliminarily causing a reaction of part of the raw material fluid M is aligned on the left side of the main reactor core 3 (on one side in the width direction of the reactor 1) via a plurality of supporting pillars 31. The pre-reactor core 29 is removably integrated with (attached to) the main reactor core 3. The pre-reactor core 29 is not necessarily integrated with the main reactor core 3 and may be separated from the main reactor core 3. When the pre-reactor core 29 is separated from the main reactor core 3, a connection member connecting the outlet side of pre-reaction flow channels 37 and the inlet side of the main reaction channels 11 is provided, so as to supply the raw material fluid from the pre-reaction flow channels 37 to the main reaction flow channels 11. In addition, a connection member connecting the outlet side of the main reaction channels 11 and the inlet side of pre-temperature control flow channels 43 is provided, so as to supply the raw material fluid from the main reaction flow channels 11 to the pre-temperature control flow channels 43.

The pre-reactor core 29 includes a plurality of (multiple) rectangular pre-reactor structures 33 for providing a reaction space for the raw material fluid M and a plurality of (multiple) rectangular pre-temperature control structures 35, the pre-reactor structures 33 and the pre-temperature control structures 35 being alternately stacked in the vertical direction. The specific configuration of each of the pre-reactor structures 33 and the pre-temperature control structures 35 is described below.

Figure 4:
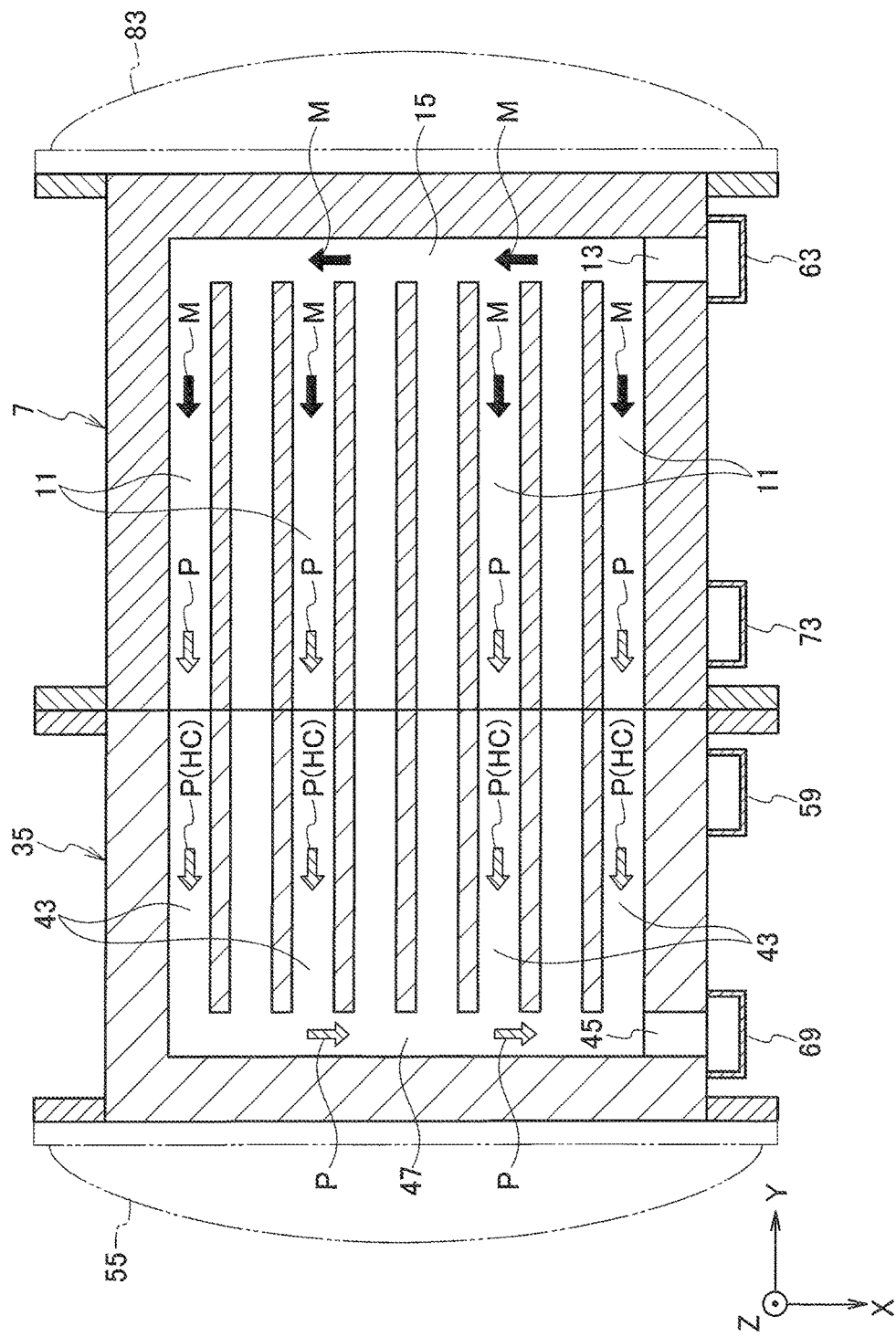
FIG. 4 is a cross-sectional view taken along line IV-IV of FIG. 1.

As shown in FIG. 2, FIG. 4, and FIG. 7, the pre-reactor structure 33 is made of the same material as the main reactor structure 7. The plural pre-reaction flow channels 37 through which the raw material fluid M flows in the right direction are arranged at regular intervals in the front-rear direction on one surface (the upper surface) of the pre-reactor structure 33. The respective pre-reaction flow channels 37 extend in the lateral direction (the width direction of the reactor 1), and have a channel length (a length in the lateral direction) which is set at approximately several tens of centimeters in the present embodiment, for example. The left side of the pre-reaction flow channels 37 corresponds to the inlet side (the introduction side) of the flow direction of the raw material fluid M, and is open so as to introduce the raw material fluid M therefrom. The right side of the pre-reaction flow channels 37 corresponds to the outlet side (the leading-out side) of the flow direction of the raw material fluid M.

The respective pre-reaction flow channels 37 have a rectangular shape in cross section. For example, in the present embodiment, the width of the pre-reaction flow channels 37 is set at 2 to 60 mm, and the height of the pre-reaction flow channels 37 is set at 1 to 10 mm, preferably 4 to 8 mm.

A raw material leading-out port 39 for leading the raw material fluid M (including part of the product P) out of the pre-reactor structure 33 is provided on the right side on the front surface of the pre-reactor structure 33. A pre-reaction connection flow channel 41 by which the raw material leading-out port 39 connects with the plural pre-reaction flow channels 37 on the right side (on the outlet side) is provided on the right side on one surface of the pre-reactor structure 33. The pre-reaction connection flow channel 41 extends in the front-rear direction.

The pre-reactor core 29 is schematically illustrated. For example, the pre-reactor core 29 includes several tens of pre-reactor structures 33 and several tens of pre-reaction flow channels 37 in each pre-reactor structure 33 in the present embodiment. The number of the pre-reaction connection flow channel 41 may be changed depending on the number of the pre-reaction flow channels 37. The maximum pressure in the respective pre-reaction flow channels 37 when the reactor 1 is in operation is set at a predetermined level in a range of 0.0 to 20.0 MPaG which varies depending on the reaction type and conditions of the raw material fluid M.

The pre-temperature control structure 35 is made of the same material as the main reactor structure 7. The plural pre-temperature control flow channels 43 through which the product P serving as a heat medium HC flows in the left direction (in the counter flow direction) opposite to the flow direction of the raw material fluid M flowing in the pre-reaction flow channels 37 are arranged at regular intervals in the front-rear direction on one surface (the upper surface) of the pre-temperature control structure 35. The respective pre-temperature control flow channels 43 extend in the lateral direction, and have a channel length (a length in the lateral direction) which is set at approximately several tens of centimeters in the present embodiment, for example. The right side of the pre-temperature control flow channels 43 corresponds to the inlet side (the introduction side) of the flow direction of the heat medium HC, and is open so as to introduce the product P serving as a heat medium HC. The left side of the pre-temperature control flow channels 43 corresponds to the outlet side (the leading-out side) of the flow direction of the heat medium HC. The inlet side (the right side) of the pre-temperature control flow channels 43 is directly connected to (directly connects with) the outlet side (the left side) of the corresponding main reaction channels 11. When the pre-reactor core 29 is separated from the main reactor core 3, the inlet side of the pre-temperature control flow channels 43 connects with the outlet side of the corresponding main reaction channels 11 by a connection member (not shown).

The respective pre-temperature control flow channels 43 have a rectangular shape in cross section. For example, in the present embodiment, the width of the pre-temperature control flow channels 43 is set at 2 to 60 mm, and the height of the pre-temperature control flow channels 43 is set at 1 to 10 mm, preferably 4 to 8 mm. The pre-temperature control flow channels 43 are opposed to the corresponding pre-reaction flow channels 37 in the vertical direction.

A product leading-out port 45 for leading the product P out of the pre-temperature control structure 35 is provided on the left side on the front surface of the pre-temperature control structure 35. A pre-temperature control connection flow channel 47 by which the product leading-out port 45 connects with the plural pre-temperature control flow channels 43 on the left side (on the outlet side) is provided on the left side of one surface of the pre-temperature control structure 35. The pre-temperature control connection flow channel 47 extends in the front-rear direction.

As described above, the pre-reactor core 29 is schematically illustrated. For example, the pre-reactor core 29 includes several tens of pre-temperature control structures 35 and several tens of pre-temperature control flow channels 43 in each pre-temperature control structure 35 in the present embodiment. The number of the pre-temperature control connection flow channel 47 may be changed depending on the number of the pre-temperature control flow channels 43. The maximum pressure in the respective pre-temperature control flow channels 43 when the reactor 1 is in operation is set at a predetermined level in a range of 0.0 to 20.0 MPaG which varies depending on the reaction type and conditions of the raw material fluid M.

As shown in FIG. 7, the lowermost pre-temperature control structure 35 is thicker than the other pre-temperature control structures 35. The respective pre-temperature control structures 35 other than the lowermost pre-temperature control structure 35 have the same dimensions as the pre-reactor structures 33. The uppermost pre-temperature control structure 35 is provided with a pre-lid structure (a pre-lid member) 49 having a rectangular plate shape and covering the pre-temperature control connection flow channels 43.

As shown in FIG. 7 and FIG. 8, a pre-catalyst member 51 supporting a catalyst for promoting the reaction of the raw material fluid M is removably provided in the respective pre-reaction flow channels 37. The pre-catalyst member 51 is made of the same material as the main catalyst member 25, and extends in the lateral direction. The pre-catalyst member 51 has a wave-like shape in cross section, for example. The catalyst may be applied on the respective pre-reaction flow channels 37, instead of the pre-catalyst member 51 removably provided in the respective pre-reaction flow channels 37.

A pair of pre-fins (pre-fin baffles) 53 is removably provided in the respective pre-temperature control flow channels 43. The paired pre-fins 53 are laid on top of each other in the vertical direction. The respective pre-fins 53 are made of the same material as the main fins 27, and extend in the lateral direction. The respective pre-fins 53 have a wave-like shape in cross section, for example.

As shown in FIG. 1 and FIG. 2, a first raw material introduction chamber (an example of hollow raw material introduction members) 55 having a dome-like shape for introducing the raw material fluid M into the respective pre-reaction flow channels 37 is removably provided on the left side of the pre-reactor core 29. The first raw material introduction chamber 55 connects with the respective pre-reaction flow channels 37. The first raw material introduction chamber 55 is provided in the middle with a first raw material supply port 57. The first raw material supply port 57 is connected to a raw material supply source (not shown) for supplying the raw material fluid M.

A raw material exhaust chamber (an example of hollow product exhaust members) 59 having a box shape for collecting and exhausting the raw material fluid M led out of the respective raw material leading-out ports 39 is provided on the right side on the front surface of the pre-reactor core 29. The raw material exhaust chamber 59 extends in the vertical direction and connects with the respective raw material leading-out ports 39. The raw material exhaust chamber 59 is provided in the middle with a raw material exhaust port 61.

A second raw material introduction chamber (an example of hollow raw material introduction members) 63 having a box shape for introducing the raw material fluid M into the respective main reaction channels 11 is provided on the right side of the main reactor core 3. The second raw material introduction chamber 63 extends in the vertical direction and connects with the respective raw material introduction ports 13. The second raw material introduction chamber 63 is provided in the middle with a second raw material supply port 65. A connection member 67 by which the outlet side of the respective pre-reaction flow channels 37 connects with the inlet side of the respective main reaction channels 11 via the raw material exhaust chamber 59 and the second raw material introduction chamber 63, is provided between the raw material exhaust port 61 and the second raw material supply port 65.

A product exhaust chamber (an example of hollow product exhaust members) 69 having a box shape for collecting and exhausting the product P led out of the respective product leading-out ports 45 is provided on the left side on the front surface of the pre-reactor core 29. The product exhaust chamber 69 extends in the vertical direction and connects with the respective product leading-out ports 45. The product exhaust chamber 69 is provided in the middle with a product exhaust port 71. The product exhaust port 71 is connected to another treatment device (not shown) for subjecting the product P to aftertreatment.

As shown in FIG. 1 and FIG. 3, a heat medium introduction chamber (an example of hollow heat medium introduction members) 73 having a box shape for introducing the heat medium into the respective heat medium introduction ports 19 is provided on the left side on the rear surface (the back surface) of the main reactor core 3. The heat medium introduction chamber 73 extends in the vertical direction and connects with the respective main temperature control flow channels 17. A heat medium supply port 75 is provided at the upper portion of the heat medium introduction chamber 73. The heat medium supply port 75 is connected to a heat medium supply source 77 for supplying the heat medium HC via a supply pipe 79. A heat medium adjustment device 81 such as a heat medium adjustment valve is installed in the middle of the supply pipe 79. The heat medium adjustment device 81 adjusts a flow rate or temperature of the heat medium HC supplied to the respective main temperature control flow channels 17 so as to set the temperature of the respective main reaction channels 11 on the outlet side (the temperature of the product P) at a target temperature. The heat medium adjustment device 81 may be omitted when the product P does not contain carbon monoxide (CO).

A heat medium exhaust chamber (an example of hollow heat medium exhaust members) 83 having a dome-like shape for collecting and exhausting the heat medium led out of the respective main temperature control flow channels 17 is removably provided on the right side of the main reactor core 3. The heat medium exhaust chamber 83 connects with the respective main temperature control flow channels 17. The heat medium exhaust chamber 83 is provided in the middle with a heat medium exhaust port 85. The heat medium exhaust port 85 is connected to a heat medium recovering apparatus (not shown) for recovering the heating fluid HC.

Next, the effects of the present embodiment and a method of producing a product according to the present embodiment including a heat exchange step and a pre-heat exchange step are described below. In the following explanations, the reaction of the raw material fluid M by the reactor 1 is an endothermic reaction for illustration purposes.

Heat Exchange Step (Main Reaction Step)

The raw material fluid M is supplied to the first raw material introduction chamber 55 (on the pre-reactor core 29 side) from the raw material supply source via the first raw material supply port 57, so that the raw material fluid M is introduced to the respective pre-reaction flow channels 37. The raw material fluid M introduced flows through the respective pre-reaction flow channels 37 in the right direction of the drawings and is led to the raw material exhaust chamber 59 through the respective raw material leading-out ports 39. The raw material fluid M led to the raw material exhaust chamber 59 is then supplied to the second raw material introduction chamber 63 through the raw material exhaust port 61, the connection member 67, and the second raw material supply port 65.

The raw material fluid M supplied to the second raw material introduction chamber 63 is introduced to the respective main reaction channels 11 through the respective raw material introduction ports 13 and flows through the respective main reaction channels 11 in the left direction of the drawings. Namely, the raw material fluid M supplied to the first raw material introduction chamber 55 is introduced to the respective main reaction channels 11 via the respective pre-reaction flow channels 37, the connection member 67, and the like and flows through the respective main reaction channels 11 in the left direction of the drawings. In addition, the heat medium HC is supplied to the heat medium introduction chamber 73 (on the main reactor core 3 side) from the heat medium supply source 77 (outside the reactor 1), so that the heat medium HC is introduced to the respective main temperature control flow channels 17 through the respective heat medium introduction ports 19 and flows through the respective main temperature control flow channels 17 in the right direction of the drawings. The heat exchange is then carried out between the raw material fluid M in the main reaction channels 11 and the heat medium HC in the corresponding main temperature control flow channels 17, so as to heat the raw material fluid M. In association with the reaction promotion due to the catalyst supported in the respective main catalyst members 25, the temperature of the raw material fluid M is increased to a reaction temperature, so as to cause a reaction (an endothermic reaction) of the raw material fluid M and produce the product P, which is led out of the outlet side of the respective main reaction channels 11 accordingly. The heat medium HC used for the heat exchange is led into the heat medium exhaust chamber 83 from the outlet side of the respective main temperature control flow channels 17, so as to be exhausted from the heat medium, exhaust port 85 toward the heat medium recovering apparatus outside the reactor 1.

Pre-Heat Exchange Step (Pre-Reaction Step)

As described above, the raw material fluid M supplied to the first raw material introduction chamber 55 is introduced to the respective pre-reaction flow channels 37, and flows through the respective pre-reaction flow channels 37 in the right direction of the drawings. The product P led out of the respective main reaction channels 11 is introduced to the respective pre-temperature control flow channels 43, and flows through the respective pre-temperature control flow channels 43 in the left direction of the drawings. The heat exchange is then carried out between the raw material fluid M in the pre-reaction flow channels 37 and the product P serving as a heat medium HC in the corresponding pre-temperature control flow channels 43, so as to preheat the raw material fluid M and cool the product P in the pre-reactor core 29. In association with the reaction promotion due to the catalyst supported in the respective pre-catalyst members 51, part of the raw material fluid M can be preliminarily reacted, and the temperature of the product P can be cooled.

The product P serving as a heat medium HC used for the heat exchange is led into the product exhaust chamber 69 through the respective product leading-out ports 45, so as to be exhausted from the product exhaust port 71 toward the other treatment device outside the reactor 1.

FIG. 9A illustrates temperature conditions when the reactor 1 is in operation (temperature conditions of the raw material fluid M, the product P, and the heat medium HC). In the pre-reactor core 29, the temperature of the raw material fluid M is increased from 350° C. to 600° C. through the heat exchange with the product P serving as a heat medium HC. In the main reactor core 3, the reaction (the endothermic reaction) of the raw material fluid M is caused through the heat exchange with the heat medium HC, so as to produce the product P at a temperature of 850° C. The heat load (the amount of heat consumed) in the pre-reactor core 29 corresponds to 30% of the heat load in the entire reactor 1, and the heat load in the main reactor core 3 corresponds to 70% of the entire reactor 1.

The length of at least one side of each of the main reaction channels 11 and the main temperature control flow channels 17 in cross section is set at several millimeters, and the specific surface area of each of the main reaction channels 11 and the main temperature control flow channels 17 per unit of volume is large. The pair of the main fins 27 can generate a turbulent flow of the heat medium HC in the respective main temperature control flow channels 17 and increase the heat transfer area inside the respective main temperature control flow channels 17. Accordingly, the heat exchange performance (the efficiency of heat transfer) between the raw material fluid M in the main reaction channels 11 and the heat medium HC in the corresponding main temperature control flow channels 17 is improved.

Similarly, the length of at least one side of each of the pre-reaction flow channels 37 and the pre-temperature control flow channels 43 in cross section is set at several millimeters, and the specific surface area of each of the pre-reaction flow channels 37 and the pre-temperature control flow channels 43 per unit of volume is large. The pair of the pre-fins 53 can generate a turbulent flow of the product P serving as a heat medium HC in the respective pre-temperature control flow channels 43 and increase the heat transfer area inside the respective pre-temperature control flow channels 43. Accordingly, the heat exchange performance between the raw material fluid M in the pre-reaction flow channels 37 and the heat medium HC in the corresponding pre-temperature control flow channels 43 is improved.

Since the product P can be cooled in the pre-reactor core 29, the reactor 1 can recover the heat to decrease the temperature of the product P, so as to sufficiently prevent an increase in the amount of the heat recovered from the product P outside the reactor 1. Particularly, since the heat exchange performance between the raw material fluid M in the pre-reaction flow channels 37 and the heat medium HC in the corresponding pre-temperature control flow channels 43 is improved, the reactor 1 can recover the heat of the product P in a short period of time.

In addition to the effects described above, the heat medium adjustment device 81 adjusts the flow rate or temperature of the heat medium HC supplied to the respective main temperature control flow channels 17, while monitoring the temperature on the outlet side of the respective main reaction channels 11. Thus, the temperature on the outlet side of the respective main reaction channels 11 (the temperature of the product P) can be set at a target temperature.

Since the main reactor core 3 can be separated from the pre-reactor core 29, the main catalyst members 25 can easily be replaced from the left side of the main reactor core 3 when the catalyst supported on the main catalyst members 25 is deteriorated. The pre-fins 53 can also easily be replaced from the right side of the pre-reactor core 29 when the pre-fins 53 are damaged. Since the heat medium exhaust chamber 83 is removably attached to the main reactor core 3 on the right side, the main fins 27 can easily be replaced from the right side of the main reactor core 3 when the main fins 27 are damaged. Since the first raw material introduction chamber 55 is removably attached to the pre-reactor core 29 on the left side, the pre-catalyst members 51 can easily be replaced from the left side of the pre-reactor core 29 when the catalyst supported on the pre-catalyst members 51 is deteriorated.

According to the present embodiment, the reactor 1 can recover the heat of the product P in a short period of time, so as to sufficiently prevent an increase in the amount of the heat recovered from the product P outside the reactor 1. Accordingly, heat energy (input energy) of the heat medium HC supplied to the main reactor core 3, namely, to the reactor 1 can be decreased and an excessive amount of steam generated outside the reactor 1 can be suppressed, so as to improve the energy efficiency of the entire plant.

Since the heat exchange performance between the raw material fluid M in the pre-reaction flow channels 37 and the product P serving as a heat medium HC in the corresponding pre-temperature control flow channels 43 is improved, the reaction speed of the raw material fluid M and the yield of the product P can be increased.

Since the temperature on the outlet side of the respective main reaction channels 11 can be set at a target temperature, metal dusting in related facilities (not shown) such as the other treatment device described above due to the product P can sufficiently be prevented even when the product P contains carbon monoxide (CO).

Since the main catalyst members 25 and the pre-fins 53 can easily be replaced from the left side of the main reactor core 3 and the right side of the pre-reactor core 29, respectively, the performance of maintenance of the reactor 1 can be improved.

FIG. 10A illustrates temperature conditions when the reactor 1 is in operation in a case in which the reaction of the raw material fluid M is an exothermic reaction.

Other Embodiments

The configuration of a reactor 1A according to another embodiment shown in FIG. 9B different from the configuration of the reactor 1 according to the embodiment described above (refer to FIG. 1 and FIG. 9A) is briefly described below.

Instead of the configuration in which the inlet side of the pre-temperature control flow channels 43 is directly connected to the outlet side (the right side) of the corresponding main reaction flow channels 11, the outlet side (the right side) of the pre-reaction flow channels 37 is directly connected to the inlet side (the left side) of the corresponding main reaction flow channels 11. While FIG. 1 and FIG. 9A illustrate the reactor 1 including the connection member 67 by which the outlet side of the pre-reaction flow channels 37 connects with the inlet side of the main reaction flow channels 11, FIG. 9B illustrates the reactor LA including a connection member 87 by which the outlet side of the main reaction flow channels 11 connects with the inlet side of the pre-temperature control flow channels 43. The product P led out of the respective main reaction flow channels 11 is introduced to the pre-temperature control flow channels 43 via the connection member 87.

FIG. 9B illustrates temperature conditions when the reactor core 1A is in operation in the case in which the reaction of the raw material fluid M is an endothermic reaction. FIG. 10B illustrates temperature conditions when the reactor 1A is in operation in the case in which the reaction of the raw material fluid M is an exothermic reaction.

Other embodiments can also achieve the same operations and effects as the embodiment described above.

The present disclosure is not intended to be limited to the description of the embodiments described above, and may be applicable to various modes. For example, more than one pre-reactor core 29 may be provided. The flow direction of the heat medium. HC flowing in the main temperature control flow channels 17 may be changed from the direction opposite to the flow direction of the raw material fluid M flowing in the main reaction flow channels 11 so that the heat medium HC flows in the same direction. The flow direction of the product P serving as a heat medium HC flowing in the pre-temperature control flow channels 43 may be changed from the direction opposite to the flow direction of the raw material fluid M flowing in the pre-reaction flow channels 37 so that the product P flows in the same direction. The case in which the flow direction of the heat medium HC flowing in the main temperature control flow channels 17 is the same as the flow direction of the raw material fluid M flowing in the main reaction flow channels 11 is illustrated below.

For example, the raw material fluid M subjected to an exothermic reaction to produce a product is supplied to the main temperature control flow channels 17. The raw material fluid HC subjected to an endothermic reaction to produce a product is supplied to the main reaction flow channels 11. As the raw material fluid M flows through the main temperature control flow channels 17, the exothermic reaction is caused to generate heat of reaction. The heat of reaction thus generated can be used for a heat source for the endothermic reaction to be caused in the main reaction flow channels 11. Accordingly, the heat can be used effectively.

For example, when the raw material fluid M is reacted at a constant temperature in the main reaction flow channels 11, a refrigerant as a raw material fluid HC is introduced to flow through the main temperature control flow channels 17 in order to keep the inlet temperature so as not to deactivate the catalyst. Accordingly, the raw material fluid M can be reacted constantly in the main reaction flow channels 11 while heat is removed so as not to deactivate the catalyst.

It should be noted that the present disclosure includes various embodiments which are not disclosed herein. Therefore, the scope of the present disclosure is defined only by the matters specified according to the claims reasonably derived from the description described above.

What is claimed is:

1. A reactor for causing a reaction of a raw material fluid by a heat exchange between the raw material fluid and a heat medium to generate a product, the reactor comprising:
 a main reactor core including a main reaction flow channel through which the raw material fluid flows and causes the reaction of the raw material fluid, and a main temperature control flow channel through which the heat medium flows along a flow direction of the raw material fluid flowing in the main reaction flow channel; and
 a pre-reactor core including a pre-reaction flow channel of which an outlet side connects with an inlet side of the main reaction flow channel and through which the raw material fluid flows, and a pre-temperature control flow channel of which an inlet side connects with an outlet side of the main reaction flow channel and through which the product serving as the heat medium flows along a flow direction of the raw material fluid flowing in the pre-reaction flow channel;
wherein
 the main reactor core includes:
  main reactor structures each provided with the main reaction flow channel; and
  main temperature control structures alternately stacked on the main reactor structures and each provided with the main temperature control flow channel;
 the pre-reactor core includes:
  pre-reactor structures each provided with the pre-reaction flow channel; and
  pre-temperature control structures alternately stacked on the pre-reactor structures and each provided with the pre-temperature control flow channel; and
 the inlet side of the pre-temperature control flow channel is directly connected to the outlet side of the main reaction flow channel.

2. The reactor according to claim 1, further comprising a connection member connecting the outlet side of the pre-reaction flow channel and the inlet side of the main reaction flow channel.

3. The reactor according to claim 1, wherein a catalyst for promoting the reaction of the raw material fluid is supported in each of the main reaction flow channel and the pre-reaction flow channel.

4. The reactor according to claim 3, wherein a main catalyst member supporting the catalyst is removably provided in the main reaction flow channel, and a pre-catalyst member supporting the catalyst is removably provided in the pre-reaction flow channel.

5. The reactor according to claim 1, wherein a main fin is removably provided in the main temperature control flow channel, and a pre-fin is removably provided in the pre-temperature control flow channel.

6. The reactor according to claim 1, further comprising a heat medium adjustment device for adjusting a flow rate or a temperature of the heat medium supplied to the main temperature control flow channel.

7. The reactor according to claim 1, wherein the pre-reactor core is removably integrated with the main reactor core.

8. The reactor according to claim 1, wherein the heat medium flows through the main temperature control flow channel in a direction opposite to or identical to the flow direction of the raw material fluid flowing in the main reaction flow channel.

9. The reactor according to claim 1, wherein the product serving as the heat medium flows through the pre-temperature control flow channel in a direction opposite to or identical to the flow direction of the raw material fluid flowing in the pre-reaction flow channel.

10. The reactor according to claim 1, wherein, in the pre-reactor core, when a temperature of the raw material fluid is increased through the heat exchange with the product serving as a heat medium, part of the raw material fluid is preliminarily reacted.

\* \* \* \* \*